United States Patent [19]
McMahon et al.

[11] Patent Number: 5,435,317
[45] Date of Patent: Jul. 25, 1995

[54] RESPIRATORY MONITOR AND STIMULUS IMPARTING DEVICE AND METHOD

[75] Inventors: Newton McMahon, Darling Point; John Spry, Thornleigh, both of Australia

[73] Assignee: Lesbar Pty Limited, New South Wales, Australia

[21] Appl. No.: 990,612

[22] Filed: Dec. 14, 1992

[30] Foreign Application Priority Data

Jun. 14, 1990 [AU] Australia .................... PK0641

[51] Int. Cl.$^6$ .................................... A61B 5/08
[52] U.S. Cl. ............................ 128/716; 128/721
[58] Field of Search ............. 128/716, 721, 722, 773; 84/DIG. 24; 174/50

[56] References Cited

U.S. PATENT DOCUMENTS

| | | |
|---|---|---|
| 2,888,086 | 5/1959 | O'Brien . |
| 3,089,130 | 5/1963 | Wilson .................. 128/716 X |
| 3,628,620 | 12/1971 | Byers . |
| 3,658,052 | 4/1972 | Alter ...................... 128/721 |
| 3,831,586 | 8/1974 | Petit ....................... 128/721 |
| 3,926,177 | 12/1975 | Hardway, Jr. et al. . |
| 3,998,209 | 12/1976 | Macuaugh ............... 128/716 |
| 4,509,527 | 4/1985 | Fraden .................... 128/721 |
| 4,619,270 | 10/1986 | Margolis et al. ........ 128/721 |
| 4,657,026 | 4/1987 | Tagg ....................... 128/721 |
| 4,788,533 | 11/1988 | Mequignon .......... 128/716 X |
| 4,889,130 | 12/1989 | Lee ...................... 128/716 X |
| 4,960,118 | 10/1990 | Pennock ................ 128/721 |

FOREIGN PATENT DOCUMENTS

| | | |
|---|---|---|
| 29545 | 3/1985 | Australia . |
| 0055345 | 7/1982 | European Pat. Off. . |
| 2427238 | 12/1979 | France . |
| 3617012 | 11/1986 | Germany . |
| 3536491 | 4/1987 | Germany . |
| 2192460 | 1/1988 | United Kingdom .... 128/721 |
| 8600996 | 2/1986 | WIPO . |

*Primary Examiner*—Lee S. Cohen
*Assistant Examiner*—Samuel Gilbert
*Attorney, Agent, or Firm*—Helfgott & Karas

[57] ABSTRACT

A device for detecting a respiratory dysfunction of a person located in a bed, cot, crib or the like, and imparting, in response to detection of cessation of respiratory function of the person within the bed, cot, crib or the like, a rocking motion to the bed, cot, crib or the like. The device comprises a detection unit which is provided under the mattress of the bed, cot, crib or the like, and a stimulation unit, which acts, in response to a signal from the detection unit, to impart a rocking motion to the bed, cot, crib or the like. The detection unit is embodied as a pad-like device provided under the mattress.

5 Claims, 4 Drawing Sheets

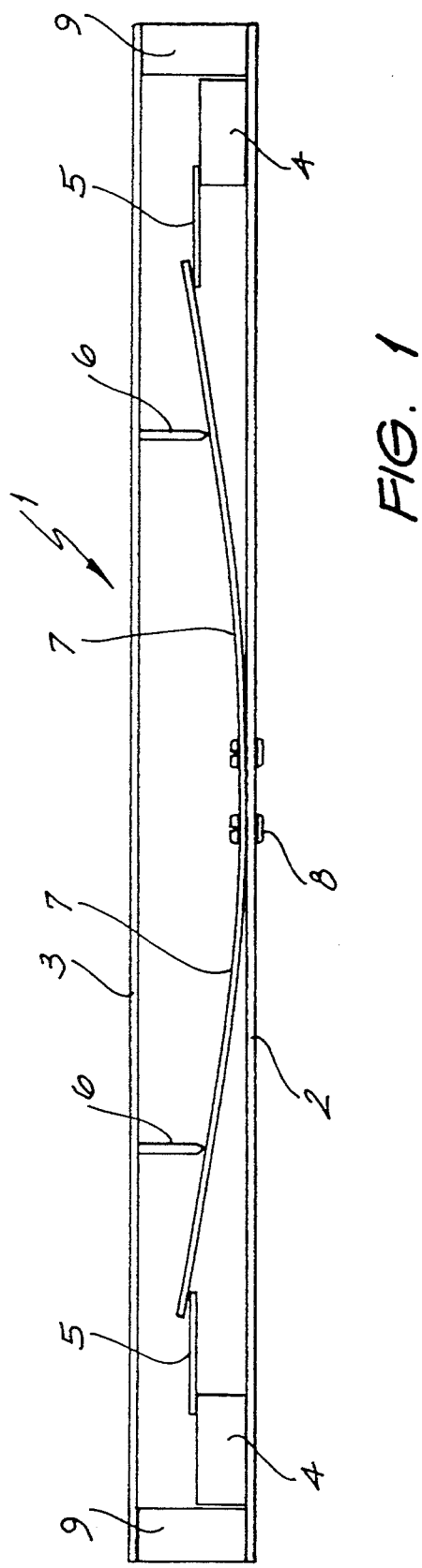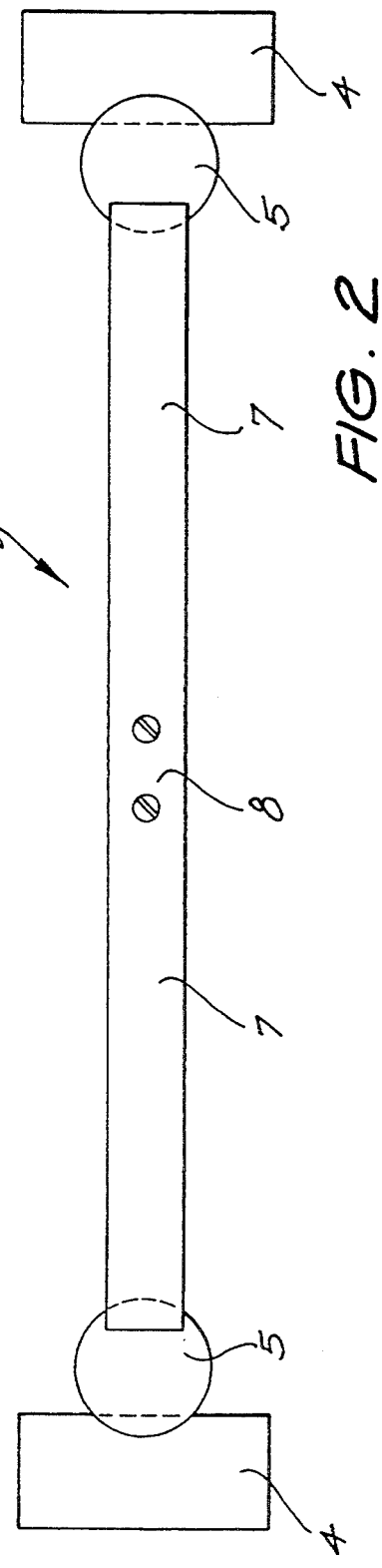

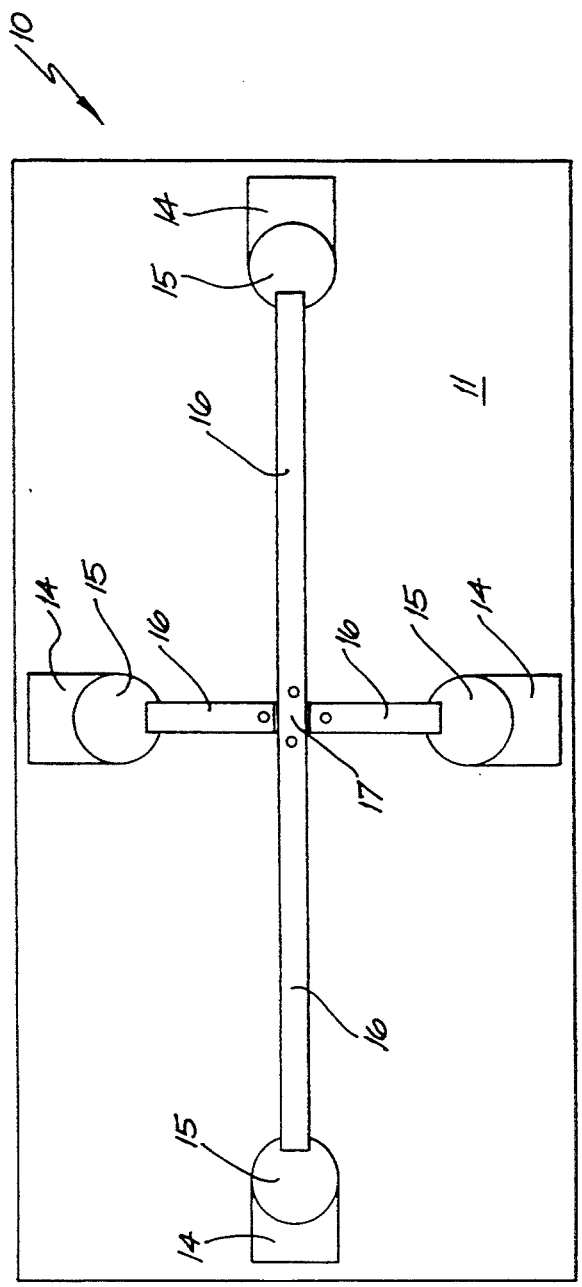
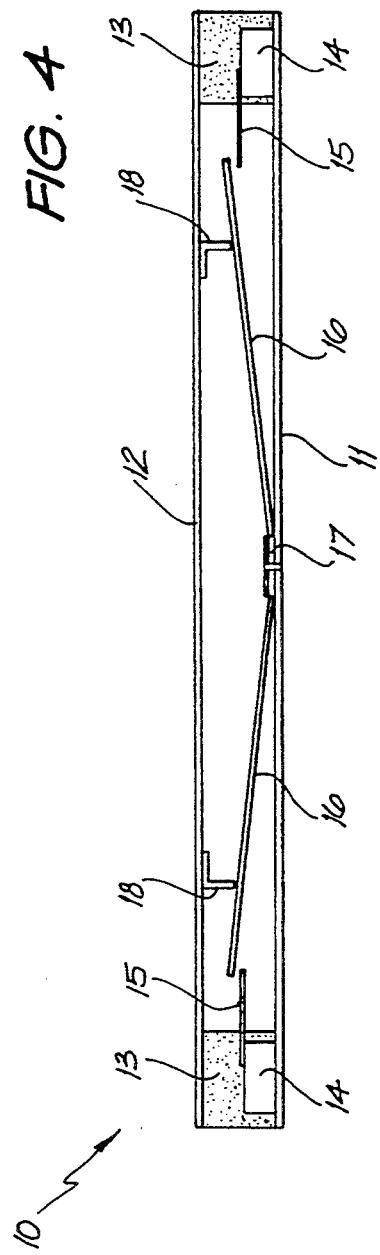
FIG. 4
FIG. 5

RESPIRATORY MONITOR AND STIMULUS IMPARTING DEVICE AND METHOD

BACKGROUND OF THE INVENTION

The present invention relates to a respiratory monitor, and in particular to an electromechanical transducer device for monitoring respiratory movements of a person, primarily for monitoring cot-death syndrome of infants.

The present invention also relates to a device and method for imparting a stimulus to a sleeping being, and in particular, to a device and method wherein the occurance of a predetermined condition may be detected, and upon detection, thereof, operate a stimulation means to consciously or subconsciously provide a stimulus to said being.

A number of devices are presently known for monitoring respiratory movements of persons, and in particular for monitoring cot-death syndrome of infants. Much of the development of such devices has been limited by the technology at hand, and in particular the technology as far as electrical transducer devices are concerned.

For instance, AU-B-29443/87 in the name of J. K. Frost relates to an electromechanical transducer for detecting movements of the human body. The invention discloses a device which comprises a compressible pad constructed of 'cellophane' material or the like, the device also having a microphone, such that during compression/expansion a noise is produced by the 'cellophane', and a signal is generated therefrom. GB-A-1469488 in the name of F. A. Chandler et al discloses a granular flow sensing and switching device, wherein, the device is utilised to detect flow by means of placing a probe with a microphone in the flow and detecting an acoustic signal. The signal is then processed to give an indication as to the flow of, for instance, grains striking the probe. An electrical capacitance device is disclosed in AU-A-73917/81, wherein a plurality or sensor members are arranged one on the other such that the variation of spacing between adjacent sheets may be measured by a measure of the variation of electrical capacitance therebetween. AU-B-58956/80 in the name of E. B. Cohen discloses a movement monitoring device comprising a tubular housing with end caps and containing a freely movable ball bearing and, according to movement of the ball, an electrical signal is supplied representative of the physical activity of a person. U.S. Pat. No. 3,875,929 in the name J. T. Grant utilises a microwave radar means which provides a movement sensitive field of microwave radiation. U.S. Pat. No. 3,926,177 in the name of E. V. Hardway also utilises a resilient capacitive pad adapted to respond to the movement of a body by providing a capacitive change.

It is therefore seen that, whilst the devices for monitoring respiratory movement are common, their advance is generally the improvement in the transducer means associated therewith, or, to an improvement in the arrangement of the particular transducer device.

In more recent times, for instance as disclosed in U.S. Pat. No. 4,359,726 in the name of J. Lewiner et al, piezo-electric transducers are utilised. The device disclosed in the abovementioned U.S. Pat. No. 4,359,726 comprises a foil interposed between two films. The foil is sensitive to pressure variations applied locally to it. AU-A-46089/85 in the name of R. Benkendorf et al also discloses the use of a piezo-electric transducer device. The construction of the Benkendorf et al device is quite complex, specifically, being a rigid base with a flexible top, between which are provided a pad. The flexible top has two rigid members, the ends being provided with a piezo-electric transducer therebetween. Upon the imposition of a force on the flexible top, which results in relative angular movement between each of the rigid members, this movement is sensed by the transducer which supplies an appropriate signal to an suitable processing circuit.

It will therefore be understood that much development has been undertaken in respect of movement detection devices, primarily associated with the advances in technology. However, despite the more recent advances, that is, the advances in respect of piezo-electric transducer devices, an efficient and sensitive device has still not yet been constructed. It will be appreciated that, particularly when the respiratory monitor is adapted to monitor cot-death syndrome, the provision of an extremely sensitive fail-safe device is imperative. Failure of a transducer to respond could well result in death of a child, and, should such a device have a low reliability by excess false triggering, an alarm signal may be prone to be ignored by an operator.

Also, various devices are known to provide some form of stimulation to persons. For example, reference is made to U.S. Pat. No. 5,002,144 by the Applicant. In this aforementioned Patent specification, there is provided a device for imparting an orbital motion to a wheeled baby carriage or cot. This device is particularly designed to provide a rocking motion, which perhaps stimulates a prenatal motion within a mother's womb. This rocking device is particularly advantageous for rocking an infant to sleep.

The present invention seeks to overcome the disadvantages of the prior art, by providing a highly sensitive and accurate monitoring device for the detection of respiratory movements of a person.

The present invention seeks to provide a device which combines these unique and different technologies in providing a device which detects the occurance of a predetermined condition such as respiratory disfunction, and upon detection of such predetermined condition, either consciously or subconsciously provide a stimulus. It will be appreciated that the provision of the stimulus then "reminds" the person or other being of the occurance of the predetermined condition such that the being then automatically either consciously or subconsciously reacts to effectively discontinue the predetermined condition.

SUMMARY OF THE INVENTION

In one broad form the present invention provides an electromechanical transducer device for monitoring respiratory movements of a person, said device comprising:
  a lower surface member being of substantially rigid construction;
  at least one support extending upwardly from said lower surface member each having a first end of a piezo-electric transducer adapted to be contacted thereby;
  an upper surface member provided in spaced apart relationship from said lower surface member and adapted to move relative thereto, and having at least one protrusion extending downwardly therefrom adapted to move each protrusion adapted to move a second end of a respective piezo-electric transducer device;

such that, any substantially vertical movement sensed by said upper surface member is transferred via said protrusion to said piezo-electric transducer(s) for generation of an electrical signal.

Preferably, the electromechanical transducer device further comprises a flexible member, pivotally supported on said lower surface member and having an end portion in contact with said second end of said piezo-electric transducer, whereby an intermediate portion thereof is contacted by one of said at least one protrusion extending from said upper surface member;

such that any vertical movement of said end portion of said flexible member and said piezo-electric transducer corresponds to vertical movement of said upper surface member and said protrusion extending therefrom.

Also, preferably, the electromechanical transducer device further comprises a flexible support means constructed of foam, rubber or the like, provided at least in the corner or end portions between said upper and lower surface members, whereby vertical movement between said surface members is allowed.

In a preferred embodiment of the present invention, the electromechanical transducer device preferably has a pair of piezo-electric transducers, each at substantially end portions of said surface members.

Also, preferably, in a preferred embodiment of the present invention the flexible member is pivotally supported in a substantially central portion thereof, with each end thereof being in contact with one of said piezo-electric transducers.

In a preferred embodiment of the invention, four piezo-electric transducers are provided, each intermediate each corner of said surface members.

In a still further preferred embodiment four piezo-electric transducers are provided, each one substantially in each corner of said surface member.

In a further broad form, the present invention provides a method of monitoring respiratory movements of a person comprising the steps of providing the electromechanical transducer device as hereinbefore described on a substantially horizontal surface, optionally providing a mattress or like apparatus thereon, and lying a person thereon to monitor said persons' respiratory movements.

In yet a further broad form, the present invention provides a device for imparting a stimulus to a person or other being, comprising:

detection means, to detect the occurance of a predetermined condition in said person or other being; and, stimulation means, to consciously or subconsciously provide a stimulus to said person or other being upon detection of said predetermined condition by said detection means.

A preferred form of the invention is one wherein said detection means is a respiratory monitor, and wherein said stimulation means provides said stimulus upon detection of cessation or alteration of respiratory function of said person or other being by said detection means.

Alternatively, another preferred form of the invention is one wherein said detection means is an audio transducer device, and wherein said stimulation means provides said stimulus upon detection of snoring noise(s) of said person or other being by said detection means.

In still a preferred form of the invention, said person or other being is asleep.

In a preferred form of the invention, said stimulation means provides an impulse to said being.

Alternatively, a preferred from of the invention is wherein said stimulation means provides a rocking motion to said being.

In a further broad form, the present invention provides a method for imparting a stimulus to a person or other being, comprising the steps of:

detecting the occurance of a predetermined event pertaining to a person or other being, utilising a detection means; and, subconsciously or consciously providing a stimulus to said person or other being upon detection of said predetermined condition by said detection means.

BRIEF DESCRIPTION OF THE DRAWINGS

The present invention will become more fully understood from the following detailed description thereof in connection with the accompanying drawing wherein:

FIG. 1 illustrates a side elevational view of an electromechanical transducer device in accordance with a preferred embodiment of the present invention;

FIG. 2 illustrates a plan view of the electromechanical transducer device as illustrated in FIG. 1;

FIG. 4 illustrates a plan view of the embodiment depicted in FIG. 3;

FIG. 5 illustrates an elevational view of the embodiment depicted in FIG. 3;

DETAILED DESCRIPTION OF THE INVENTION

Figure 3:
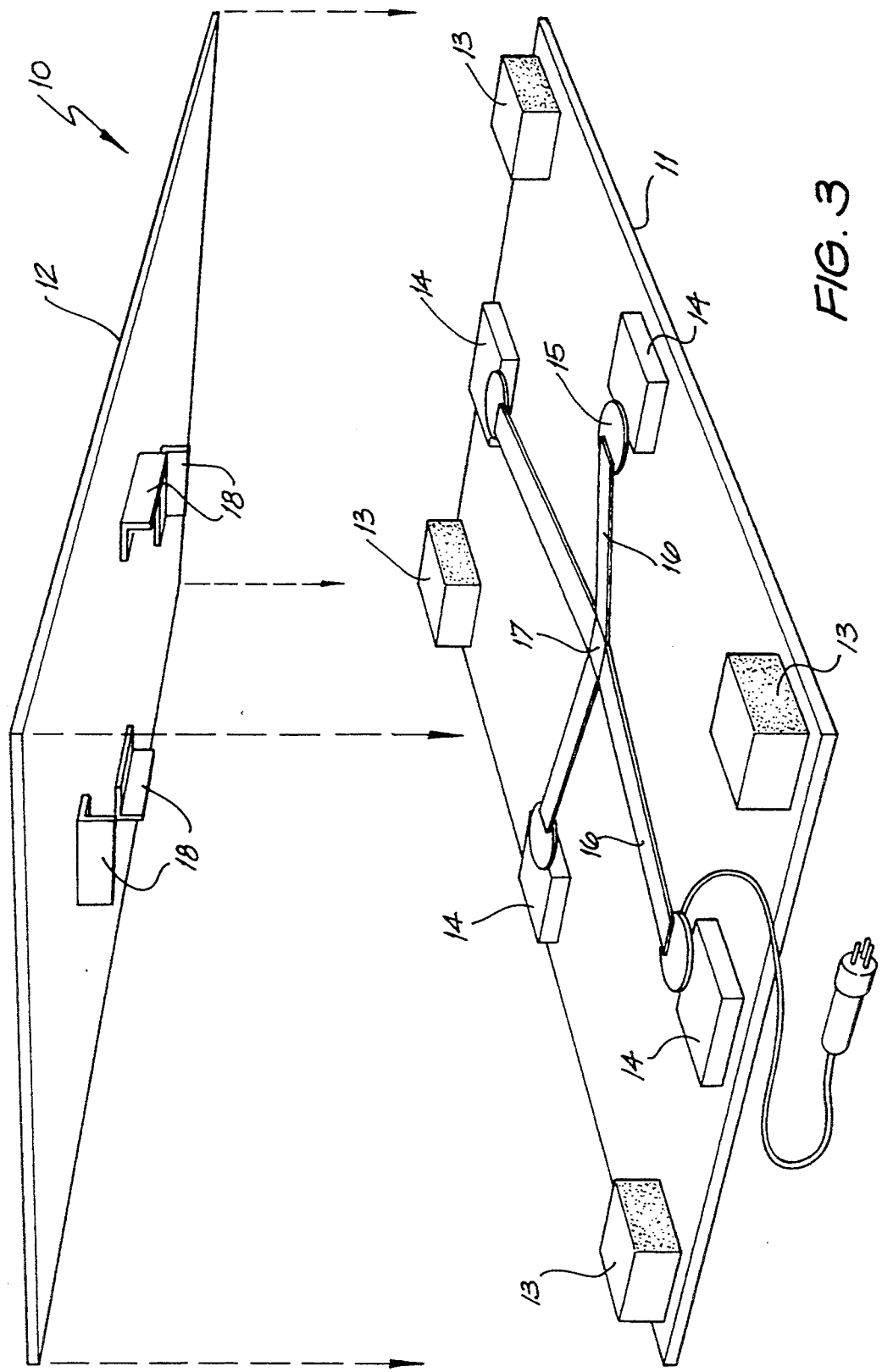
FIG. 3 illustrates an exploded perspective view of a four-transducer device in accordance with an alternatively preferred embodiment of the present invention.

The electromechanical transducer device as illustrated in FIGS. 1 or 2, generally designated by the numeral 1, comprises a lower surface member 2, preferably rigid in construction, and an upper surface member 3 is spaced apart relationship form the lower surface member 2, preferably spaced apart by means of at least two flexible support members 9, at each end or in the corners of the two surface members 2 and 3. A pair of supports, 4, one at each end on the lower surface member 2 are provided, and, to one side of the upper end of each support 4, is connected a piezo-electric transducer device 5. The other end of the piezo-electric transducer device 5 is adapted to be connected either directly or indirectly to the upper surface member 3, by means of a protrusion, designated 6, extending downwardly therefrom. Such protrusion 6 may either be directed immediately from the upper surface member 3 to the second end of the piezo-electric transducer device 5, or, as shown in FIGS. 1 and 2, may be connected indirectly via a flexible member 7. The flexible member 7 is shown as being pivotally connected to the lower surface member 2 at a fulcrum point 8. The flexible member may be constructed of semi-rigid plastics material or the like.

By providing a flexible member such as this, rather than by directly connecting the protrusion 6 from the upper surface member 3 to the second end of the piezo-electric transducer device 5, a more sensitive device is obtained. That is, should the lower tip portion of the protrusion 6 move a certain distance, then, the end portion of the flexible member 7, will move approximately twice the distance. Therefore, any minute movement on the upper surface member 3 will be transmitted and effectively amplified by means of a flexible member to the piezo-electric device 5. As with conventional piezo-electric transducing devices, an electrical current is generated with the movement of the device. Such electric current may be supplied to appropriate circuitry to activate an alarm, should lack of respiratory movement and consequential lack of movement of upper plate 3 detected.

The electromechanical transducer device as illustrated in FIGS. 3, 4 and 5, generally designated by the numeral 10, comprises a lower surface member 11, preferably rigid in construction, an upper surface member 12 in spaced apart relationship from the lower surface member 11, shown spaced apart by four compressible blocks 13, for instance, constructed of foam plastics material, in each corner, between the two surface members 11 and 12. Intermediate the corners of the lower surface member 11, are shown four rigid transducer mounting blocks 14. Connected to one side of the upper end of each block 14 is a piezo-electric transducer device 15. The other end of the piezo-electric transducer device 15 being adapted to be connected either directly or indirectly to the upper surface member 12. In the case shown in FIGS. 3, 4 and 5, flexible lever arms 16 are provided, connected at the ends thereof to the piezo-electric transducer device 15, and intermediate their ends (forming fulcrum point) to the rigid base 11. Intermediate the fulcrum point 17 and the ends of the lever arms 16, the contacts or protrusions 18 are adapted to engage therewith. These contacts are shown connected to the upper plate 12 and extending downwardly therefrom. Obviously, alternative arrangements of connecting the upper plate 12 to the second end of the piezo-electric transducer devices 15 (either directly or indirectly) will be envisaged. It will be appreciated that the flexible lever arms 16 are preferably constructed of semi-rigid plastics material or the like. By providing flexible arms such as this rather than by directly connecting the protrusion 18 from the upper surface member 12 to the second end of the piezo-electric transducer device 15, a more sensitive apparatus is obtained. That is, should the lower tip portions of the protrusions 18 move a certain distance, then the end portions of the arms 16 will move approximately twice the distance or some proportion thereof, depending on how close to the transducer devices 15 the lever bars 18 contact the arms 16. Consequently, any minute movement of the upper surface 12 is transmitted and amplified by means of the arms 16 to the piezo-electric devices 15.

Figure 6:
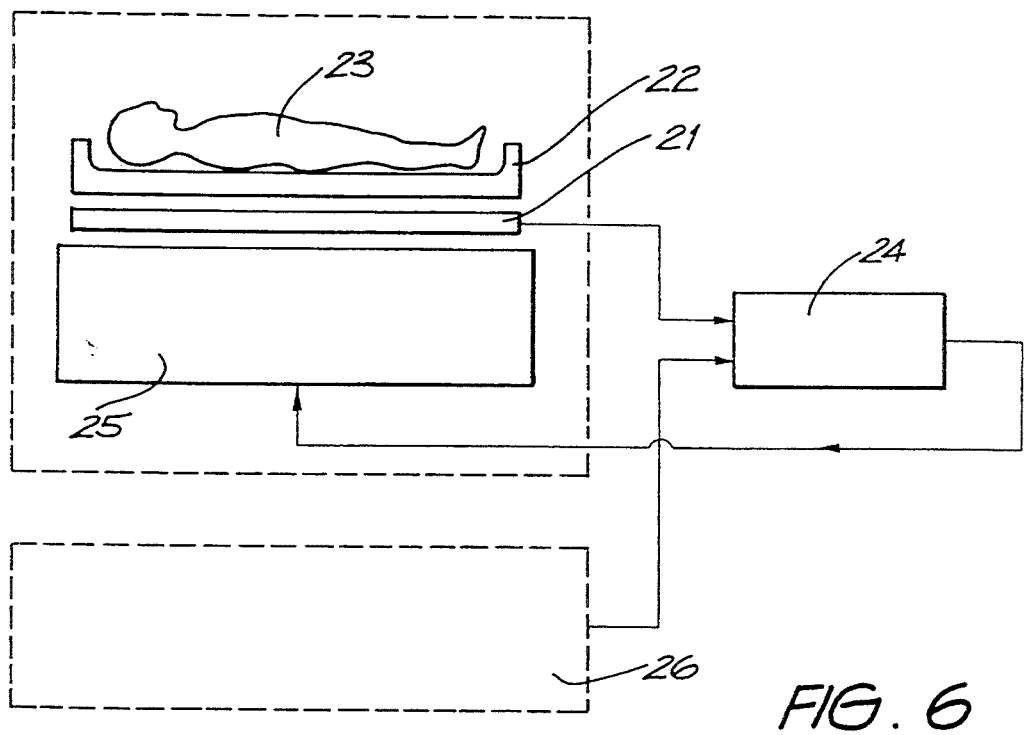
FIG. 6 illustrates a device adapted for monitoring the respiratory disfunction of an infant, and providing suitable stimulation in the event that such disfunction is detected.

In FIG. 6 is illustrated a device for detecting respiratory disfunction of an infant, and providing a suitable stimulation means to "remind" the infant to breath, in the event that such respiratory disfunction is monitored. A suitable detection means 21 is provided on the underside of a mattress 22 upon which an infant 23 lies. The detection means 21 may for example be embodied as the respiratory monitor described in the FIGS. 1 to 5. The detection means 21 is accordingly provided to monitor the respiratory movement, and in particular, the respiratory disfunction of the infant 23, and provide a suitable signal indicative thereof to a suitable processing means 24. Also provided as an input to the processor 24 are "predetermined conditions" which may for example be electronic representations of signals indicative of respiratory disfunction. This could obviously alternatively be provided in some form of memory device in the processor. Once suitable processing is performed, in the event that the detector is deemed to detect the occurrence of such conditions indicative of respiratory disfunction, a suitable signal is provided to a stimulation means 25. The stimulation means may for example be embodied as a device which imparts an impulse to the infant 23 by jolting or rocking the infant 23. Other forms of stimulation to 'wake' the infant will become obvious to persons skilled in the art. Consequently, it will be seen that an entire system is envisaged, by which respiratory disfunction can be monitored, and in the even that respiratory disfunction occurs, a stimulation is provided to "remind" the infant to breath, consequently retaining the life of the infant.

Whilst the above embodiment has been described in connection with respiratory disfunction, the device need not necessarily have to monitor such an extreme condition. For example, instead of respiratory disfunction, the movement or sound of crying of a baby or other respiratory function may be monitored. Upon detection of the function being monitored, for example, the waking of the baby, which again is calculated by comparing the signals received from the detection means 21 with the predetermined conditions 26, stimulation in the form of providing rocking motion or impulse to the mattress 22 of the sleeping apparatus can be envisaged to be performed rock or soothe the baby back to sleep.

It will be appreciated that such a rocking device may be embodied as described in the Applicant's U.S. Pat. No. 5,002,144, the disclosures of which are incorporated in entirity into the present specification.

Figure 7:
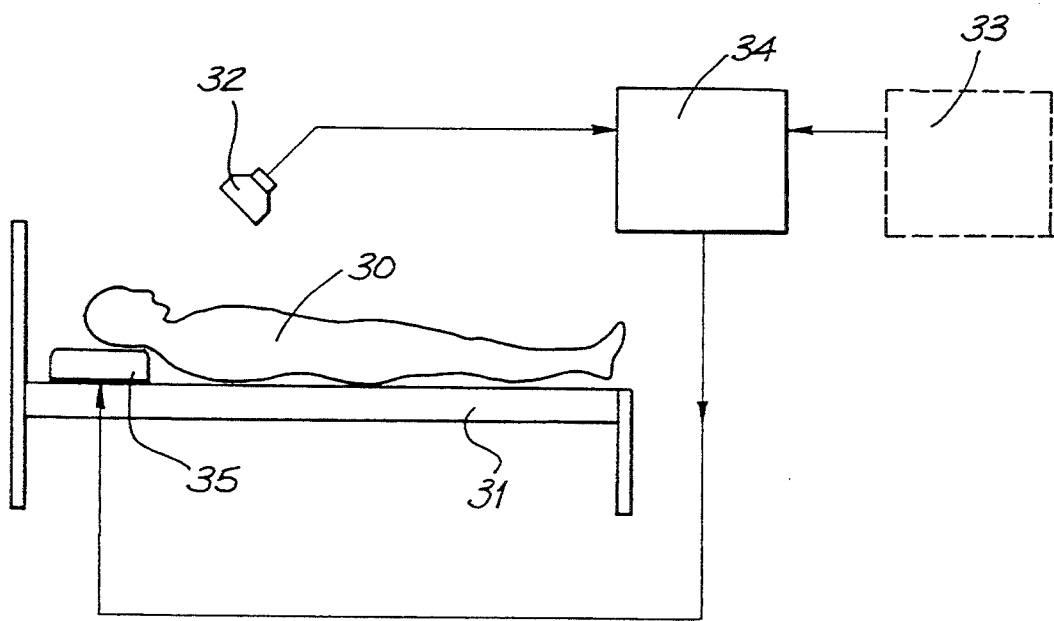
FIG. 7 illustrates a device for monitoring the snoring of a person a providing suitable stimulus to the person in the event that such snoring is monitored.

A further application for the device for imparting the stimulus is shown in FIG. 7. In FIG. 7, is shown a person 30 sleeping on a bed 31, having an audible detection means or microphone 32, provided in a receiving location, adjacent to a persons head. The microphone 32 is designed to receive audio signals such as "snoring". Since it would be appreciated that other noises might occur in the room in which the person is asleep, the persons sleeping pattern would typically be defined in electronic terms by having predetermined conditions 33 compared with the signal received from the detection means 32 in a processor 34. In the event that the signals from the detection means 32 are identified as being indicative of snoring, an electronic signal representative of this is provided from the processor 34 to the stimulation means 35. The stimulation means 35 may for example be a pillow device which may, for example, provide a jolt to the persons head such that the person 30 is "reminded" either consciously or subconsciously that he is snoring. The effect of the stimulation means, reminding the person in this manner is that the person moves to an alternative position whereat he will not snore.

It will be appreciated that numerous variations and modifications to the device as hereinbefore described will become apparent to persons skilled in the art.

It will be understood that the present invention provides a much more sensitive respiratory monitor than the prior art devices, and in particular to the prior art associated with piezo-electric transducing devices, such as disclosed in U.S. Pat. No. 4,359,726 and AU-A-46089/85.

It will be also appreciated that numerous types of stimulation means, and detection means may be provided for other applications for similar device as herein described for imparting a stimulus to a person or other being.

It will be understood by persons skilled in the art that suitable transducer devices, alternative forms of electronic circuitry for the detection means, stimulation means and processing apparatus may also be embodied.

All such variations and modifications to the present invention should however be considered to fall within the spirit and the scope of the invention as broadly described hereinbefore and as claimed hereinafter.

We claim:

1. An electromechanical transducer system, the system comprising:
    (a) a support device selected from the group consisting of a bed, cot, and crib, said support device including a mattress;
    (b) detection means for detecting the occurrence of a predetermined condition in a person or other being, provided under said mattress of said support device, wherein said detection means includes;
    a substantially rigid lower surface member;
    an upper surface member provided in spaced-apart relationship from said lower surface member; and
    at least one piezo-electric transducer means, provided intermediate of and operatively connected to each said surface member, for generating a signal in response to movement of said upper surface member relative to said lower surface member;
    (c) a processing circuitry coupled to said detection means for processing said signal so that any lack of movement of said upper surface member relative to said lower surface member, which is indicative of respiratory dysfunction of said person or other being, is detected by said piezo-electric transducer means and processed by said processing circuitry for generation of an electrical signal indicative of said respiratory dysfunction; and
    (d) stimulation means, coupled to said processing circuitry and connected to said support device for imparting, in response to said electrical signal indicative of said respiratory dysfunction, a rocking motion to said support device, wherein the entire electromechanical transducer device is arranged so as to be out of physical contact with the person or other being located in said support device and wherein said piezo-electric transducer means is connected to one of said surface members via a flexible member pivotally supported on one of said surface members, having an end portion in contact with one end of said piezo-electric transducer means and said piezo-electric transducer means is connected to another of said surface members via a rigid protrusion extending therefrom.

2. An electromechanical transducer system as claimed in claim 1, comprising a pair of said piezo-electric transducer means, respectively located at substantially edge portions of said surface members.

3. An electromechanical transducer system as claimed in claim 2, wherein said flexible member is pivotally supported in a substantially central portion thereof, with each end thereof being in contact with one of said piezo-electric transducer means.

4. An electromechanical transducer system as claimed in claim 1, wherein four of said piezo-electric transducer means are provided, each positioned along an edge portion of said upper and lower surface members and intermediate each corner of said upper and lower surface members, respectively.

5. An electromechanical transducer system as claimed in claim 1, wherein said stimulation means is arranged so as to provide a rocking motion to the mattress.

* * * * *